US012605080B2

(12) United States Patent
Haddad et al.

(10) Patent No.: US 12,605,080 B2
(45) Date of Patent: Apr. 21, 2026

(54) ADAPTIVE PULSE WAVE ANALYSIS FOR BLOOD PRESSURE MONITORING

(71) Applicant: Senbiosys, Neuchatel (CH)

(72) Inventors: Serj Haddad, Lausanne (CH); Assim Boukhayma, Neuchâtel (CH); Antonino Caizzone, Milvignes (CH)

(73) Assignee: Senbiosys, Neuchatel (CH)

( * ) Notice: Subject to any disclaimer, the term of this patent is extended or adjusted under 35 U.S.C. 154(b) by 421 days.

(21) Appl. No.: 17/455,540

(22) Filed: Nov. 18, 2021

(65) Prior Publication Data

US 2022/0175257 A1 Jun. 9, 2022

Related U.S. Application Data

(60) Provisional application No. 63/123,149, filed on Dec. 9, 2020.

(51) Int. Cl.
| | |
|---|---|
| *A61B 5/021* | (2006.01) |
| *A61B 5/00* | (2006.01) |
| *A61B 5/024* | (2006.01) |

(52) U.S. Cl.
CPC ...... *A61B 5/02108* (2013.01); *A61B 5/02416* (2013.01); *A61B 5/7225* (2013.01); *A61B 5/7253* (2013.01)

(58) Field of Classification Search
CPC . A61B 5/021; A61B 5/02108; A61B 5/02416; A61B 5/07; A61B 5/7225; A61B 5/7253
See application file for complete search history.

(56) References Cited

U.S. PATENT DOCUMENTS

| | | | | |
|---|---|---|---|---|
| 5,533,511 A | * | 7/1996 | Kaspari | A61B 5/02007 |
| | | | | 600/494 |
| 5,797,395 A | * | 8/1998 | Martin | A61B 5/029 |
| | | | | 600/526 |
| 10,912,464 B2 | * | 2/2021 | Priyankara | A61B 5/02007 |
| 11,229,404 B2 | * | 1/2022 | Rundo et al. | A61B 5/7264 |
| 2011/0009755 A1 | * | 1/2011 | Wenzel | A61B 5/0215 |
| | | | | 600/485 |
| 2013/0030267 A1 | * | 1/2013 | Lisogurski | A61B 5/14553 |
| | | | | 600/324 |
| 2015/0320364 A1 | * | 11/2015 | Knoll | A61B 5/725 |
| | | | | 600/494 |

(Continued)

FOREIGN PATENT DOCUMENTS

WO WO 2016/138965 A1 9/2016

OTHER PUBLICATIONS

N. Hasanzadeh, M. M. Ahmadi and H. Mohammadzade, "Blood Pressure Estimation Using Photoplethysmogram Signal and Its Morphological Features," in IEEE Sensors Journal, vol. 20, No. 8, pp. 4300-4310, Apr. 15, 15, 2020, doi: 10.1109/JSEN.2019. 2961411. (Year: 2020).*

(Continued)

*Primary Examiner* — Christopher Koharski
*Assistant Examiner* — Helene Bor
(74) *Attorney, Agent, or Firm* — HoustonHogle LLP

(57) ABSTRACT

An adaptive processing of the pulsatility signal can improve the pulse wave analysis (PWA) leading to a better blood pressure estimation. The technique is based on transforming the pulsatility signal so that the fiducial points required for the PWA are well-defined.

15 Claims, 7 Drawing Sheets

(56)  References Cited

U.S. PATENT DOCUMENTS

2017/0181648 A1*  6/2017  Ohno ................... A61B 5/7278
2019/0167200 A1*  6/2019  Jang ..................... A61B 5/7221
2019/0380592 A1*  12/2019  Priyankara et al. ........................
                                        A61B 5/02007

OTHER PUBLICATIONS

Xu, Lisheng et al., "Morphology variability of radial pulse wave during exercise". Bio-Medical Materials and Engineering 24 (2014) 3605-3611. (Year: 2014).*

Yan, W.-R., et al., "Cuffless Continuous Blood Pressure Estimation from Pulse Morphology of Photoplethysmograms," IEEE Access, 7: 141970-141977 (2019).

Slapničar, G., et al., "Blood Pressure Estimation from Photoplethysmogram Using a Spectro-Temporal Deep Neural Network," Sensors, 19(3420) 1-17 (2019).

International Preliminary Report on Patentability, mailed on Jun. 22, 2023, from International Application No. PCT/IB2021/060714, filed on Nov. 18, 2021, 10 pages.

Hasanzadeh, N., "Blood Pressure Estimation Using Photoplethysmogram Signal and Its Morphological Features," IEEE Sensors Journal, 20(8): 4300-4310 (2020).

Mangathayaru, N., et al., "Heart Rate Variability for Predicting Coronary Heart Disease Using Photoplethysmography," 4th International Conference on I-SMAC: 664-671 (2020).

Sasso, A.M., et al., "HYPE: Predicting Blood Pressure from Photoplethysmograms in a Hypertensive Population," Computer Vision—ECCV 2020: 325-335 (2020).

Yang. S., et al., "Blood Pressure Estimation with Complexity Features from Electrocardiogram and Photoplethysmogram Signals," Optical and Quantum Electronics, 53: 1-16 (2020).

International Search Report and Written Opinion of the International Searching Authority, mailed on Feb. 11, 2022, from International Application No. PCT/IB2021/060714, filed on Nov. 18, 2021. 17 pages.

* cited by examiner

+ Raw PPG Smoothing
+ Beat Detection
+ SQI Generation

+ Trough Identification
+ Detrending
+ Normalization

+ Signal Transformation
to Generate Artificial
Fiduciary Points

- Final PPG
- Troughs
- SQI's

Feature Extraction and Mapping

ADAPTIVE PULSE WAVE ANALYSIS FOR BLOOD PRESSURE MONITORING

RELATED APPLICATIONS

This application claims the benefit under 35 USC 119(e) of U.S. Provisional Application No. 63/123,149, filed on Dec. 9, 2020, which is incorporated herein by reference in its entirety.

BACKGROUND OF THE INVENTION

Hypertension is a long-term medical condition in which the blood pressure (BP) in the arteries is persistently elevated. It is the main risk factor for cardiovascular diseases and a major cause of premature death worldwide.

Different pulsatility signals (PS) were proposed to be used for BP monitoring. The sensors used to get pulsatility signals include reflective or transmission photoplethysmography (PPG), impedance sensors, implanted PPG, accelerometer sensors, etc. These sensors can be placed in different body locations. For example, PPG sensors can be placed on the wrist, the finger, or the ear, impedance sensors can be placed on the wrist, the chest, or the arm, and the implantable sensors can be placed in the vicinity of an artery.

In the past decade, PPG, which utilizes a light-emitting diode (LED) to illuminate the skin and measures the power of either the transmitted or the reflected light, attracted the most interest for different vital sign estimation. It is deployed in most of the mainstream wearable devices and smart phones.

Many studies confirm the accuracy of PPG-based solutions to monitor heart rate (HR) and heart rate variability (HRV), stress levels, irregularity in heart beats, sleep quality, etc. Naturally, it was also suggested as a cheap, unobtrusive technique for continuous BP estimation. This optical solution measures the variations in the volume of the blood flow. For BP monitoring, PPG-based methods rely on either pulse wave velocity (PWV) techniques or pulse wave analysis (PWA) methods.

The arterial stiffness directly affects the blood pressure. The stiffening of the arteries increases the velocity of the pressure wave propagation through the arterial tree and results in an increased blood pressure. PWV techniques aim at estimating the blood pressure by computing the propagation velocity. Some of these techniques estimate the pulse transit time (PTT), which is the time delay between proximal and distal arterial waveforms and is inversely proportional to the PWV. This can be achieved using two PPG sensors in two different body locations. Other techniques, known as pulse arrival time (PAT) techniques replace the transit time estimation by the interval estimation from the electrocardiogram (ECG) R-peak to the pulse arrival at the peripherals.

Different characteristic points on the PPG pulse waveform can be considered as the pulse arrival location. Since the time interval starts from the R-peak of the ECG, the PAT includes both the PTT and the cardiac pre-ejection period (PEP). Despite these differences, the main goal of both techniques is to accurately compute the PWV since it is strongly correlated with the blood pressure.

One of the main challenges for the PWV techniques is that the peripheral arterioles or the terminal arteries lack the elasticity that the central arteries have. For this reason, the PWV techniques fail to maintain the good performance they deliver for the central arteries when they are deployed at the body peripherals. Moreover, PPG-based BP monitoring solutions that rely on the PWV techniques require the use of auxiliary sensors, which limits its practicality and usability. Contrary to the PPG-based PWV techniques, the PPG-based pulse wave analysis (PWA) relies solely on PPG signals.

PWA technique used to estimate blood pressure is based on the PS (PPG in this case). It involves a morphological analysis of the PPG pulse waveform to extract features that can be used to estimate the blood pressure. Several time-related and amplitude-related features are proposed in the state-of-the-art. The extracted features are then mapped to blood pressure values using different techniques, such as multiple linear regression (MLR), artificial neural networks (ANN), support vector machine (SVM), random forests (RF), etc.

It is also worth mentioning that with the increasing interest in deep learning techniques, recent works have suggested PWA techniques using raw PPG signals as input to deep neural networks (DNN), without the need for explicit feature extraction.

SUMMARY OF THE INVENTION

The present invention concerns adaptive processing of the PS to improve the pulse wave analysis (PWA) leading to a better blood pressure estimation. The technique is based on transforming the PS so that the fiducial points required for the PWA are well-defined.

Stepping back, the PWA technique estimates blood pressure values by mapping the time- and amplitude-related features of the PS to BP values. A possible PS can be acquired from PPG sensors, but such signal could be obtained from other sources. The extraction of these features requires the identification of fiducial points on the PS. However, it may happen that the morphology of the PS is distorted due to aging or highly elevated blood pressure. A distorted pulsatility morphology hinders the identification of the characteristic points necessary for feature extraction, and thereby undermines the blood pressure estimation out of the PS. For this reason, the PWA techniques are accompanied with pulsatility quality assessments to discard signals with undesired morphologies.

In general, according to one aspect, the invention features a method for translating pulsatility signals, comprising: receiving input pulsatility signals from a photoplethysmography sensor; applying a signal transformation to the pulsatility signals to produce target pulsatility signals; and generating blood pressure values from the target pulsatility signals by referencing fiducials in the target pulsatility signals.

Generally, the signal transformation adds the fiducials into the target pulsatility signals with respect to the input pulsatility signals.

In examples, the signal transformation employs a Chebyshev filter whose pass-band ripple introduces artificial fiduciary points.

Also, the process may include discarding pulsatility signals with low signal quality.

Preferably, the blood pressure values are generated by applying a mapping function to estimate the blood pressure values.

Different mapping functions could be applied for different time windows of pulsatility signals.

In general, according to one aspect, the invention features a system for translating pulsatility signals, comprising a photoplethysmography sensor for generating input pulsatility signals and a computer system that applies a signal transformation to the input pulsatility signals to produce target pulsatility signals and generates blood pressure values from the target pulsatility signals by referencing fiducials in the target pulsatility signals.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The extracting time- and amplitude-related features of the pulsatility signal is hindered for certain patients and under certain scenarios. See W. Yan, R. Peng, Y. Zhang and D. Ho, "Cuffless Continuous Blood Pressure Estimation from Pulse Morphology of Photoplethysmograms," IEEE Access, doi: 10.1109/ACCESS.2019.2942936; and G. Slapničar, N. Mlakar and M. Luštrek, "Blood Pressure Estimation from Photoplethysmogram Using a Spectro-Temporal Deep Neural Network," Sensors (Basel, Switzerland), doi:10.3390/s19153420.

The present approach adapts the PWA to the input pulsatility signal (PS). In other words, instead of deploying PWA on the original pulsatility signal PS, it is deployed on a mapped/transformed version of the pulsatility signal, namely target pulsatility signal (TPS). The mapping must ensure that all the required fiducial points are well-defined and easy to identify by the PWA technique.

Figure 1:
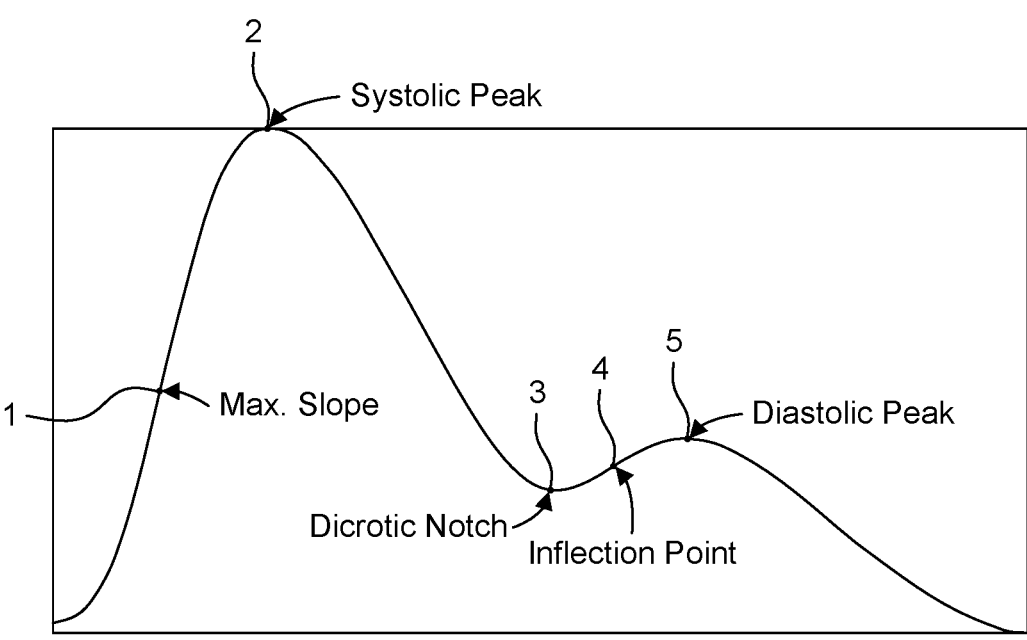
FIG. 1 is a plot of a PS showing common fiducial points.

FIG. 1 shows a pulsatility signal and common fiducial points (1, 2, 3, 4, 5).

The approach comprises two different functionalities:

For the first functionality, in each window of PS a fixed signal mapping/transfer function (MF) processing guarantees with high probability that most of the TPS's contain all the required points.

$$PS(1), \dots, PS(N) \longrightarrow \boxed{MF} \longrightarrow TPS(1), \dots, TPS(N)$$

Here, the fixed mapping function MF processing block takes the input pulsatility signals (PS(i), i=1, . . . , N) and outputs the target pulsatility signals (TPS(i), i=1, . . . , N). The signal mapping function is chosen based on a predefined window of PSs to ensure the following condition: the ratio $R_{MF}$ of the number of TPS's possessing the necessary fiducial points to the total number of pulsatility signals is above a predefined value. The mapping function remains the same with the moving window of new PS's if the stated condition remains satisfied. Otherwise, a feedback scheme is used to modify the parameters of the signal mapping function to adapt to the input pulsatility signals until the required condition is satisfied.

Figure 2:
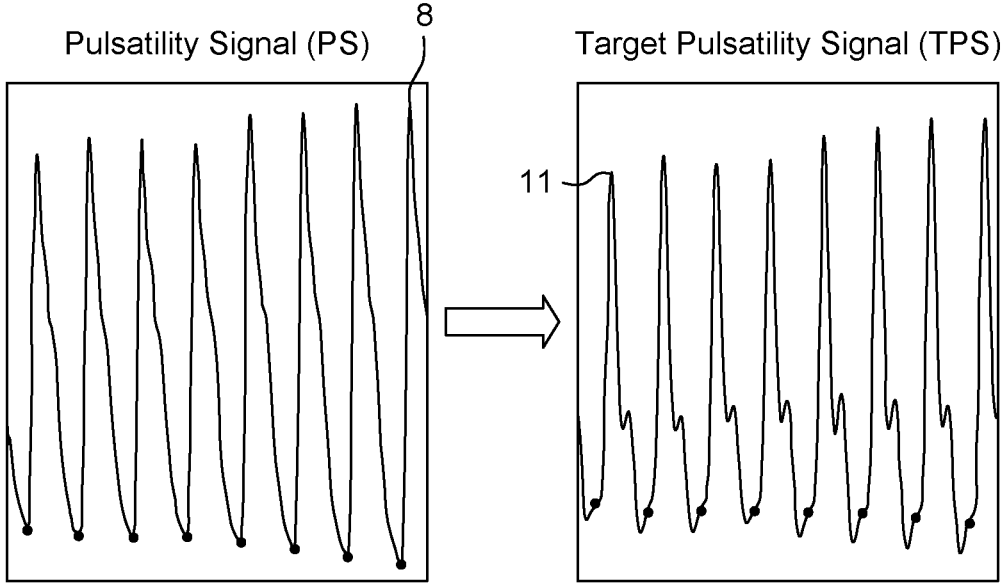
FIG. 2 is a schematic diagram showing a time window containing 7 PS's and their transformation to 7 target PS's.

As shown in FIG. 2, a window containing 7 PS's 8 (separated by a dot at the signal minima) is processed by a specific mapping function processing block to generate 7 TPS's 11. All the TPS's ($R_{MF}$=1) possess the fiducial points (1, 2, 3, 4, 5) specified in FIG. 1., while the PS's do not.

After the pulsatility signal transformation, the PWA proceeds in a conventional fashion.

Note that every time the signal mapping function is modified the BP estimation algorithm should be re-calibrated.

Figure 3:
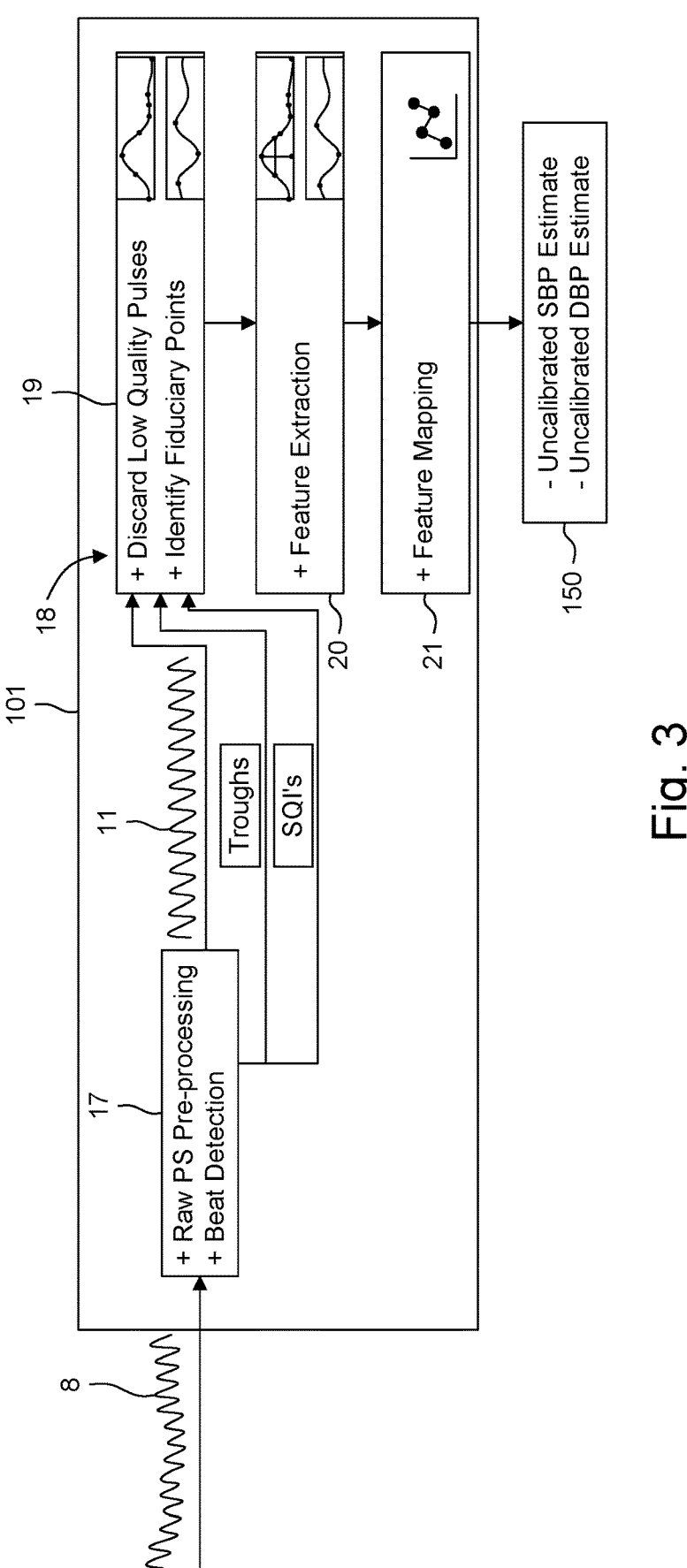
FIG. 3 is a block diagram of a blood pressure estimator for translating the input PS into uncalibrated blood pressure values according to one embodiment.
Figure 10:
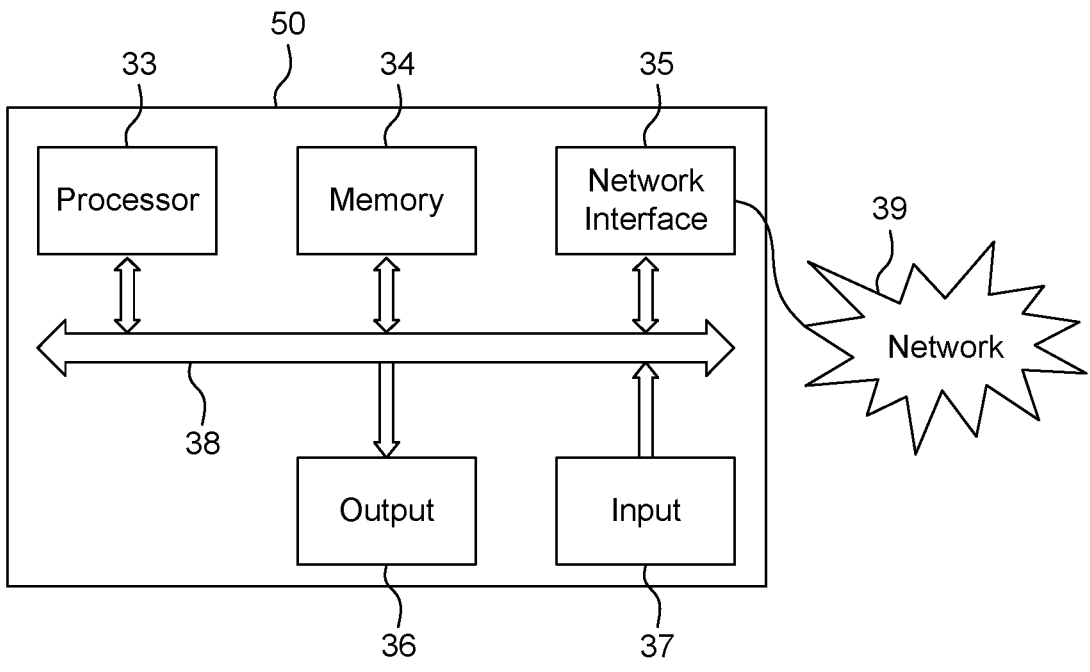
FIG. 10 is a schematic diagram of a generalized representation of an exemplary computer system, wherein the exemplary computer system is adapted to perform the instructions and operations as in this invention.

FIG. 3 shows a blood pressure estimator 101 for translating the input PS into uncalibrated blood pressure values, i.e., an uncalibrated systolic blood pressure estimate and uncalibrated diastolic blood pressure estimate 150. This estimator 101 executes on a main processing device and specifically its processor 33 as shown in FIG. 10.

Specifically, a pre-processing and beat detection signal analysis process 17, extract of the relevant features from the processed PPG signal and a feature extraction and mapping signal analysis process 18 maps those features to pressure values by discarding low quality pulses. This is achieved by identifying fiducials points 19, extracting features 20 and performing feature mapping 21. This approach enables PPG-based blood pressure monitoring (BPM) algorithms that perform the pulse wave analysis to generate the systolic and diastolic BP (SBP, DBP) estimates 150.

Figure 4:
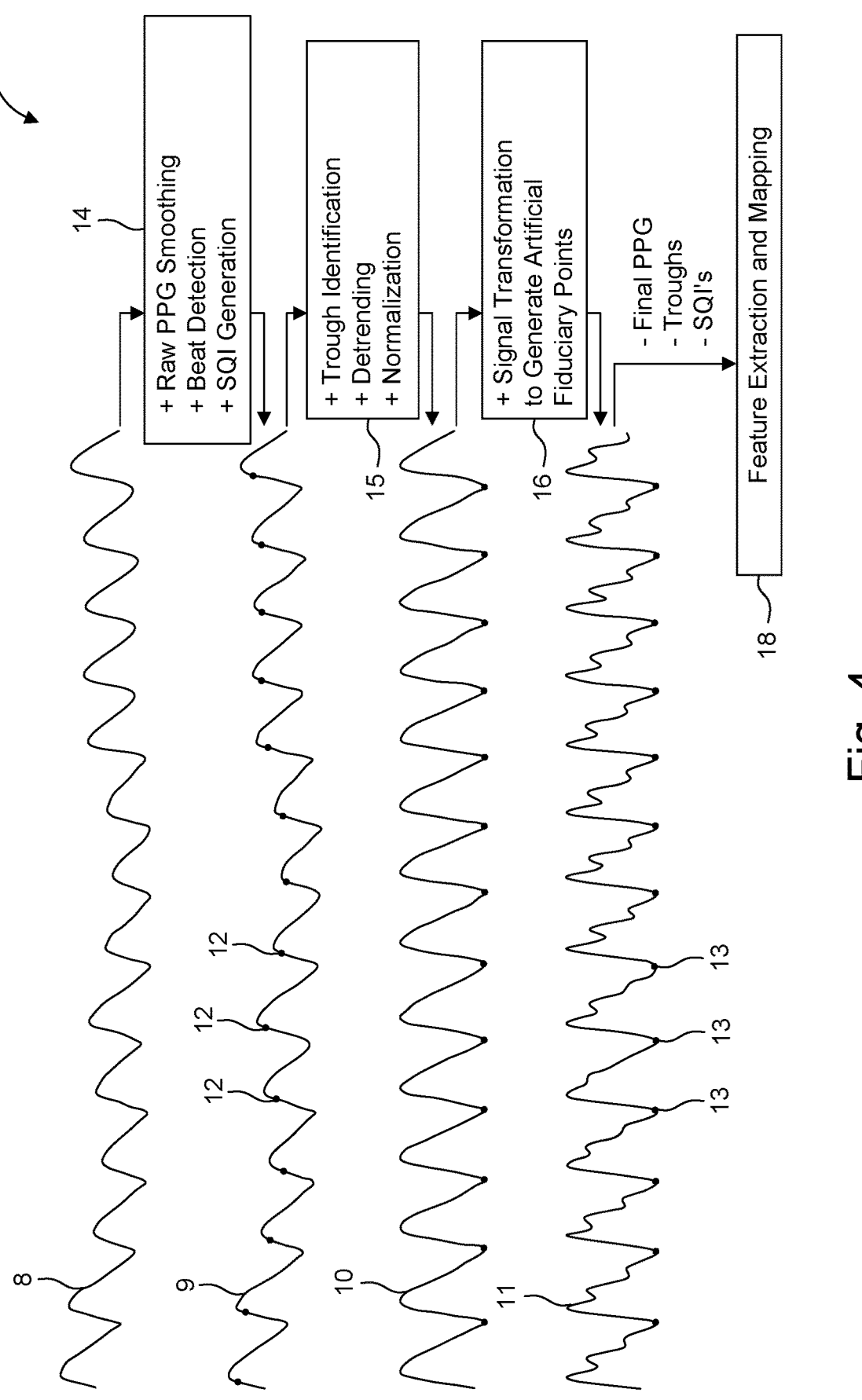
FIG. 4 is a plot schematically showing beat detection and pre-processing of the PS to generate segmented PS with the necessary morphology for PWA together with a signal quality index (SQI)

FIG. 4 shows the operation of the pre-processing and beat detection signal analysis process 17.

First, a smoothing subprocess step 14 starts by denoising the input PPG signal 8 acquired using the PPG sensor. Then, the PPG pulses are identified using the beat-to-beat detection algorithm. Each of the detected beats is associated with a signal quality index (SQI). The SQI values represent the quality of the PPG signal.

The beat detection algorithm calculates the first derivative of the PPG signal and then detects the peaks of the first derivative of the PPG signal which represent the maximum up-slopes 12 of the processed PPG signal 9. Then a normalization subprocess 15 is performed. It further identifies the troughs 13 by finding the global minimums between the consecutive maximum up-slope points. After identifying the troughs 13, the PPG signal is detrended and normalized to amplitude one to produce signal 10 by the normalization subprocess 15.

PPG pulses recorded on flexible arteries (young and healthy subjects) have very clear distinct features with all the necessary fiduciary points. On the contrary, pulses recorded from stiffer arteries (elderly and unhealthy subjects) show fewer or less distinctive features or may even lack the fiduciary points and show no features at all, as is the case in the example demonstrated in FIG. 4 and signal 10. This means the feature extraction sub-block 18 of the PPG-based BPM algorithm would typically simply discard all the recorded data because they lack the necessary features required to generate pressure values.

For this reason, the PPG signal undergoes another stage of transformation in artificial fiducial creation subprocess 16. This subprocess executes the signal mapping/transfer function (MF) processing described previously. In one embodiment, a low-pass second order type I Chebyshev filter whose pass-band ripple introduces artificial fiduciary points is employed in the mapping function. The filtered signal is then re-normalized to produce the signal 11 that is forwarded to the feature extraction and feature mapping signal analysis process 18.

Figure 5:
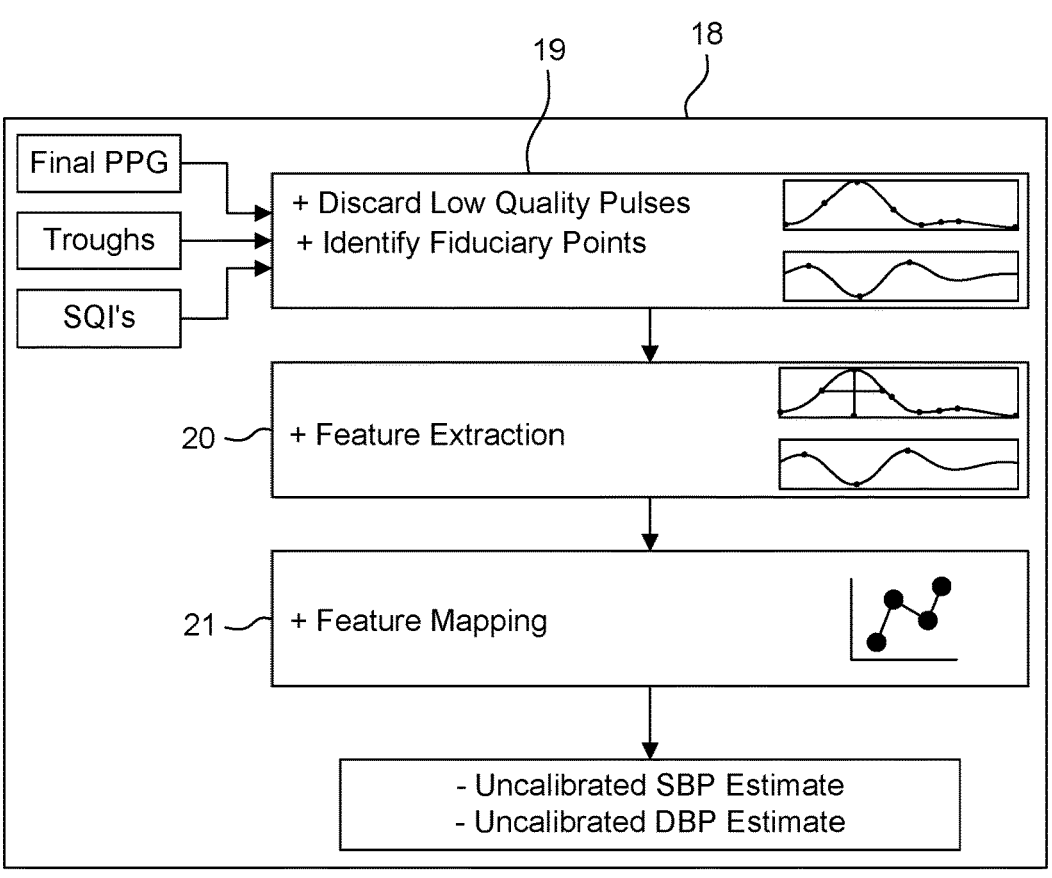
FIG. 5 is a plot of the feature extraction and mapping sub-blocks of the PWA.

FIG. 5 shows the feature extraction and mapping signal analysis process 18. As shown, it includes the subprocesses of the PPG-BPM algorithm.

Fiducial identification subprocess 19 discards the PPG pulses that have low SQI values. Afterwards, the fiducial identification subprocess 19 identifies the fiduciary points of the remaining PPG pulses. These features are based, for examples, but not limited to, on the following fiduciary points: the maximum slope on the up-rise, the systolic peak, the dicrotic notch, the inflection point, the diastolic peak, and the five acceleration PPG (APPG—the second derivative of the PPG) waves 'a', 'b', 'c', 'd', and 'e'. Using the identified fiduciary points, several time-related and amplitude-related features, which are widely used in the literature, are derived by a feature extraction subprocess 20. Finally, these features can be mapped to pressure values using, for instance, different regression models by a feature mapping subprocess 21, one to generate SBP values and another to generate DBP values. Given that the generated BP estimates are based on the volumetric changes in the blood flow and not on a real pressure signal, they require further calibration and thus said to be uncalibrated BP estimates.

Another approach to adaptive PWA is that in each window of PS's a different mapping function is identified for each PS such that all TPS's (to a great extent) have the same characteristic points.

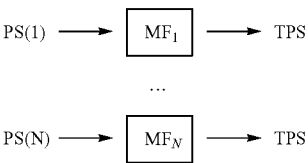

Here, for each input pulsatility signal PS(i), i=1, . . . , N, a specific mapping function $MF_i$ is identified such that the target pulsatility signal TPS remains the same as much as possible. We should note that the TPS's may not be identical, but they must be very similar, and they must have the same fiducial points.

Figure 6:
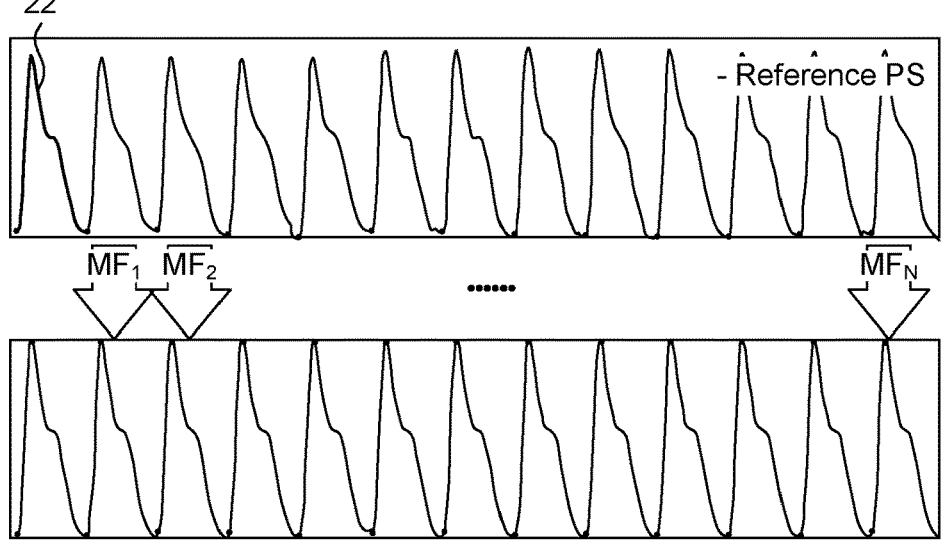
FIG. 6 shows a window containing several PS's and their transformation to target PS's in which the first PS serves as the reference PS.

FIG. 6 illustrates this functionality. A processing block chooses the first PS 22 to serve as the reference pulsatility signal which is the target pulsatility signal TPS. For each of the remaining pulsatility signals, a mapping function is identified to transform it to the chosen TPS 22. Before generating the mapping functions, each of the pulsatility signals is normalized so that its amplitude is equal to 1 and is resampled using, for example, 200 points. To identify the mapping functions MF_1, . . . , MF_N, the processing block may use (as an example) the dynamic time warping (DTW) algorithm. The algorithm computes the similarity between two temporal sequences which may have different speeds. It aligns the input pulsatility signal with the target pulsatility signal 22. The output of the algorithm is a vector containing the indices of the input PS that match to the indices of the TPS. The identified vector represents the mapping function of the given PS.

Note that with this functionality, the processing block can have non-overlapping moving windows, where the first PS of each window serves as a TPS whose reference BP value is known and it serves as a calibration value.

Figure 7:
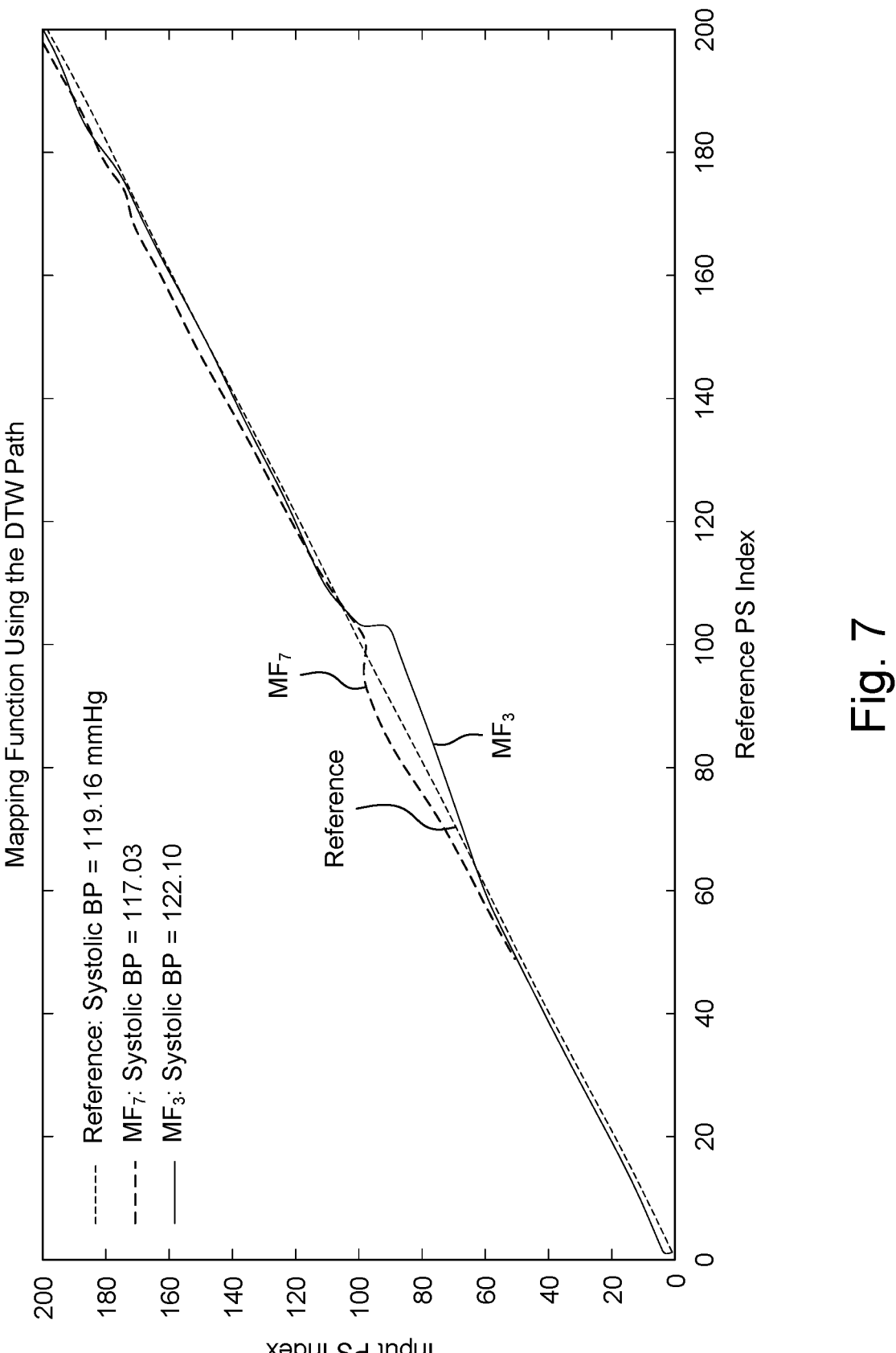
FIG. 7 is a plot of the mapping functions that match each reference PS index to a corresponding input PS index.

FIG. 7 is a plot of the mapping functions corresponding to PS(3) and PS(7) (PS(i) in FIG. 6). As mentioned, the mapping function is the DTW path of the PS and the reference PS (or TPS).

In this functionality, the mapping function processing block is used to estimate the blood pressure values from the pulsatility signals. In other words, the PWA uses the mapping function (the DTW path) to estimate the blood pressure values. Different techniques could be used to map the DTW path to BP estimates, such as using deep learning techniques to map the DTW path to BP values or extracting features from the DTW path and mapping them to BP values using different regression models.

Figure 8:
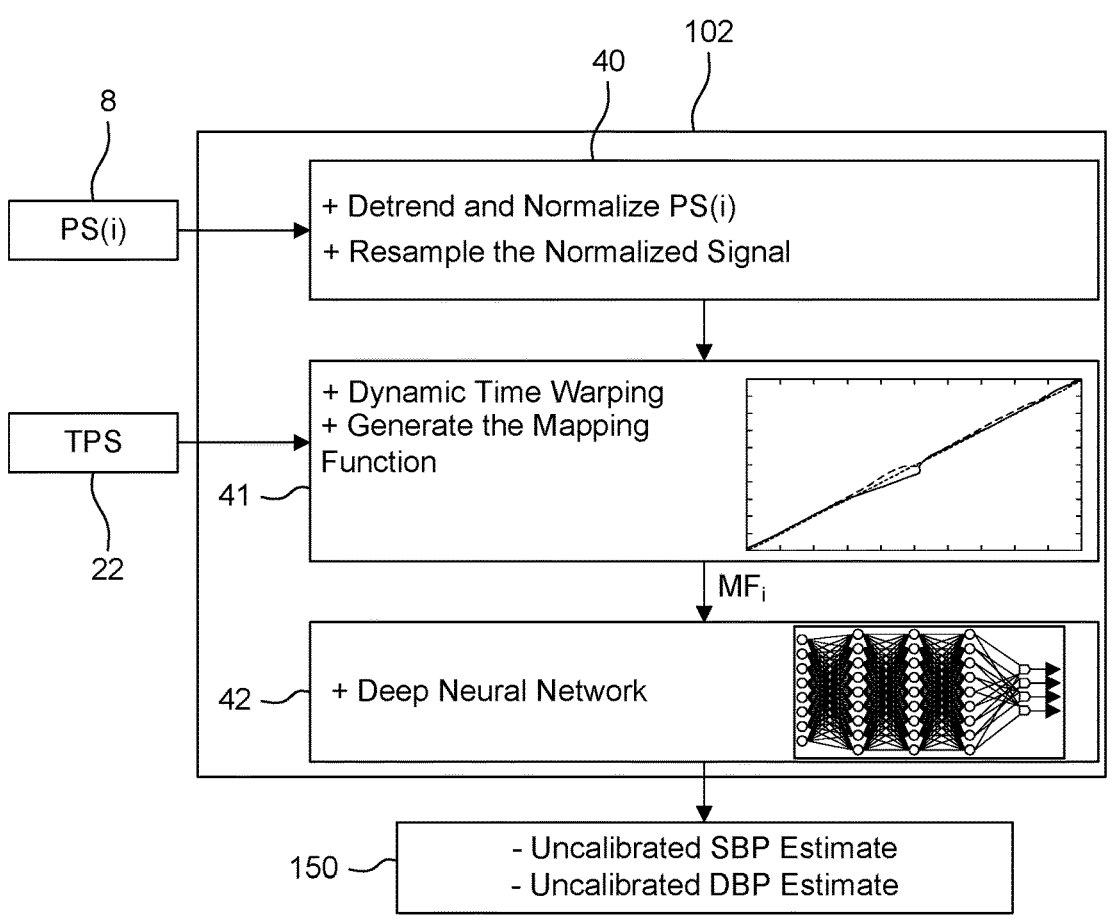
FIG. 8 is a block diagram of a blood pressure estimator translating the input PS into uncalibrated blood pressure values according to another embodiment.

FIG. 8 shows a blood pressure estimator 102 for translating the input PS into uncalibrated blood pressure values, i.e., an uncalibrated systolic blood pressure estimate and uncalibrated diastolic blood pressure estimate 150, according to another embodiment. This estimator 102 executes on a main processing device and specifically its processor 33 as shown in FIG. 10.

In this embodiment the input PS(i) is detrended, normalized, and resampled in a block 40 using, for example, 200 sample points. Then, the resulting signal and the TPS signal, which are produced by the pre-processing and beat detection signal analysis process 17 in some examples, are fed into the DTW block 41 to generate the feature mapping function MFi. Finally, the resulting mapping function is input to the deep neural network in block 42 to generate the BP values 150.

The adaptive pulse wave analysis can be implemented offline on the collected pulsatility data or online in the embodiment containing the pulsatility sensor.

The periodic variations are typically generated by the arrival of a pressure pulse at the given segment of the arterial tree. In one embodiment, the pulsatility sensor is a PPG sensor. The PPG sensor can be transmission-based or reflection-based.

Figure 9:
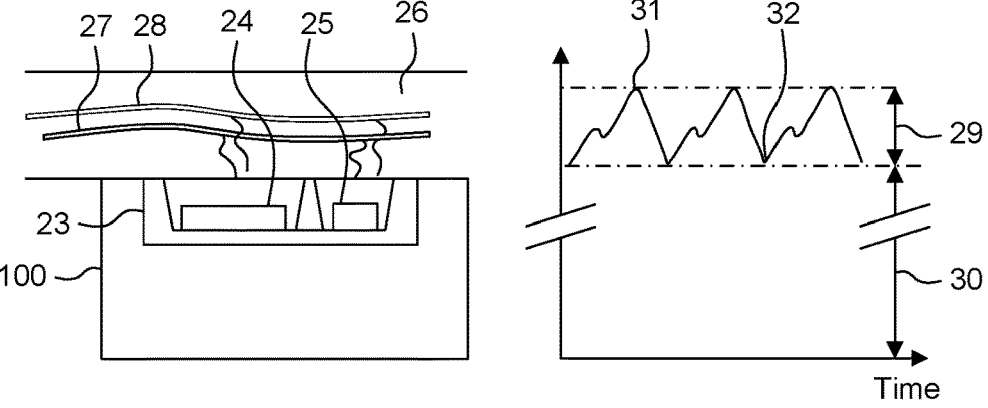
FIG. 9 shows a device with a reflective PPG pulsatility sensor.

FIG. 9 shows an example PPG apparatus 100 with a reflective PPG sensor 23, although a transmissive setup could also be employed. The apparatus 100 can be realized in an earbud, wrist or ring device. Other embodiments, including, but not limited to, chest patches are also possible. The PPG sensor 23 embeds a light source 25 and a light detector 24. Multiple light sources and light detectors are also possible. The PPG sensor is in contact with the skin 26 of a user. Different body locations are possible, including, but not limited to, the finger, the wrist and the ear canal. Due to the pulsatility of blood flow through the tissue in the subcutaneous vasculature and blood vessels 27 and 28, the perfusion index of the skin changes. This is defined as the ratio between the AC component 29 of the reflective signal and the DC component 30. The superimposition of 29 and 30 builds the pulsatile signal PS 8 that is input into the blood pressure estimator 101 shown in FIG. 3 or 102 in FIG. 8, for example. Points 31 and 32 represent the systolic and diastolic points, respectively, of the signal, resulting from the light absorption in the skin 26 as illustrated by the Beer-Lambert law.

FIG. 10 shows an exemplary computer system 50 for processing pulsatility signals and executing and implementing the processes and subprocesses described in FIGS. 3-8. This computer system 50 in some embodiments is implemented in the PPG apparatus 100 of FIG. 9 or can be arranged in another device connected with it such as, for example but not limited to, the earbud, wrist or ring device (e.g. by a cable or a wireless connection) or a smartphone.

It has to be clear that the computer system 50 can be part of the apparatus 100 or even external to it, thanks to a wired or wireless connection. The computer system 50 comprises a main processing device, the processor, 33, a main memory 34 (stating and dynamic, e.g., read-only memory (ROM), flash memory, dynamic random-access memory (DRAM) such as synchronous DRAM (SDRAM), flash memory, static random-access memory (SRAM), etc.), which may communicate with each other via the data bus 38. The processing device 33 represents one or more general-purpose processing devices such as a microprocessor, central processing unit, or the like. More specifically, different computing schemes are possible, including, but not limited to, very long instruction work (VLIW) microprocessor, reduced instruction set computing (RISC), a field programmable gate array (FPGA) processor or an application specific integrated circuit (ASIC).

The computer device also integrates a network interface 35 to interface it with an external network 39. The same computer device may or may not include an input 37 and an output 36. The input can be used to communicate inputs and selections to the computer device, via, but not limited to, a keyboard and/or a mouse. The output can include, but it is not limited to, a display unit (e.g. a light emitting diode (LED) or a liquid crystal display (LCD)).

The computer device 50 also integrated a bus 38 (and I/Os) to allow digital exchanges between the blocks.

It is also noted that the operational steps described in any of the exemplary embodiments herein are described to provide examples and discussion. The operations described may be performed in numerous different sequences other than the illustrated sequences. Furthermore, operations described in a single operational step may be performed in a number of different steps. Additionally, one or more operational steps discussed in the exemplary embodiments may be combined.

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for estimating blood pressure, comprising:
   a photoplethysmography (PPG) sensor for generating input pulsatility signals, each input pulsatility signal having fiducial points; and
   a computer system that for each input pulsatility signal of a plurality of input pulsatility signals within a pulsatility window:
     associates a translation mapping function with said input pulsatility signal such that applying the associated translation mapping function to said input pulsatility signal produces a corresponding target pulsatility signal (TPS), such that TPSs generated within the pulsatility window have same fiducial points, and
     applies the associated translation mapping function to the input pulsatility signal to produce the corresponding TPS; and
   wherein the computer system generates blood pressure values from the associated translation mapping functions.

2. The system of claim 1, wherein each associated translation mapping function adds the fiducial points into the corresponding TPSs with respect to the associated input pulsatility signals.

3. The system of claim 1, wherein at least one associated translation mapping function employs a Chebyshev filter whose pass-band ripple introduces artificial fiducial points.

4. The system of claim 1, wherein the computer system discards translated pulsatility signals with signal quality below a predetermined threshold.

5. The system of claim 1, wherein the computer system applies a blood pressure estimation mapping function to estimate the blood pressure values.

6. The system of claim 1, wherein the computer system applies different translation mapping functions for different time windows of input pulsatility signals.

7. The system of claim 1, wherein dynamic time warping is used to identify the associated translation mapping function.

8. The system of claim 1, further comprising:

a processing block that selects a first pulsatility signal from the plurality of input pulsatility signals to serve as a reference pulsatility signal, and for each of the remaining input pulsatility signals, identifies said signal's corresponding associated mapping function to transform said signal to match the reference pulsatility signal.

9. The system of claim 8, wherein the processing block further uses dynamic time warping to identify the associated translation mapping function.

10. The system of claim 1, wherein the PPG sensor is a reflective PPG sensor.

11. The system of claim 1, wherein the PPG sensor comprises multiple light sources.

12. The system of claim 1, wherein the PPG sensor comprises multiple light detectors.

13. The system of claim 1, wherein the fiducial points comprise one or more of a maximum slope on an up-rise, a systolic peak, a dicrotic notch, an inflection point, a diastolic peak, and/or acceleration photoplethysmogram (APPG) waves a, b, c, d, and e.

14. A method for estimating blood pressure, comprising:

receiving input pulsatility signals from a photoplethysmography sensor;

for each input pulsatility signal within a pulsatility window associating a translation mapping function with said input pulsatility signal such that applying the associated translation mapping function to said input pulsatility signal produces a corresponding translated pulsatility signal (TPS), such that TPSs generated within the pulsatility window have the same fiducial points;

applying the associated translation mapping function to said translation mapping function's associated input pulsatility signals to produce a corresponding translated pulsatility signal (TPS); and generating blood pressure values by mapping fiducial points in the TPSs within the pulsatility window to blood pressure values.

15. The method of claim 14, wherein dynamic time warping is used to identify the associated translation mapping function.

* * * * *